US011607487B2

(12) United States Patent
Klemm et al.

(10) Patent No.: US 11,607,487 B2
(45) Date of Patent: Mar. 21, 2023

(54) MEDICAMENT DELIVERY DEVICE

(71) Applicant: Sanofi-Aventis Deutschland GMBH, Frankfurt am Main (DE)

(72) Inventors: Thomas Klemm, Frankfurt am Main (DE); Dietmar Hammen, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 882 days.

(21) Appl. No.: 16/471,935

(22) PCT Filed: Dec. 21, 2017

(86) PCT No.: PCT/EP2017/084143
§ 371 (c)(1),
(2) Date: Jun. 20, 2019

(87) PCT Pub. No.: WO2018/115310
PCT Pub. Date: Jun. 28, 2018

(65) Prior Publication Data

US 2019/0307954 A1 Oct. 10, 2019

(30) Foreign Application Priority Data

Dec. 23, 2016 (EP) .................................... 16206615

(51) Int. Cl.
*A61M 5/155* (2006.01)
*A61M 5/142* (2006.01)
(Continued)

(52) U.S. Cl.
CPC ........ *A61M 5/155* (2013.01); *A61M 5/14248* (2013.01); *A61M 5/30* (2013.01);
(Continued)

(58) Field of Classification Search
CPC .... A61M 5/30; A61M 5/155; A61M 5/14248; A61M 5/3007; A61M 2005/3022;
(Continued)

(56) References Cited

U.S. PATENT DOCUMENTS

2003/0065294 A1* 4/2003 Pickup ................ A01K 13/003
604/304
2004/0162470 A1 8/2004 Tu
(Continued)

FOREIGN PATENT DOCUMENTS

CA 2380671 10/2003
CN 101312760 11/2008
(Continued)

OTHER PUBLICATIONS

International Preliminary Report on Patentability in International Appln. No. PCT/EP2017/084143, dated Jun. 25, 2019, 9 pages.
(Continued)

*Primary Examiner* — Tiffany Legette
(74) *Attorney, Agent, or Firm* — Fish & Richardson P.C.

(57) ABSTRACT

The present disclosure relates to a medicament delivery device comprising a medicament receiving element, at least one fluid chamber having a fluid outlet configured to direct fluid vapour towards the medicament receiving element, a heating element for heating the fluid in the at least one fluid chamber. The device is configured such that, in use, the heating element heats the fluid in the at least one fluid chamber to at least partially evaporate the fluid so that the vapor pressure in the at least one fluid chamber increases until the fluid is expelled out of the at least one fluid chamber through the fluid outlet towards the medicament receiving element and entrains the medicament towards the patient's skin.

19 Claims, 3 Drawing Sheets

(51) Int. Cl.
*A61M 5/30* (2006.01)
*A61K 38/28* (2006.01)

(52) U.S. Cl.
CPC ........... *A61M 5/3007* (2013.01); *A61K 38/28* (2013.01); *A61M 2005/3022* (2013.01); *A61M 2205/3337* (2013.01); *A61M 2205/3633* (2013.01); *A61M 2205/3653* (2013.01); *A61M 2205/50* (2013.01); *A61M 2205/8231* (2013.01); *A61M 2230/201* (2013.01)

(58) Field of Classification Search
CPC .............. A61M 15/008; A61M 15/025; A61M 2230/201; A61M 2205/3563; A61M 37/00
See application file for complete search history.

(56) References Cited

U.S. PATENT DOCUMENTS

| | | | |
|---|---|---|---|
| 2004/0260234 A1 | 12/2004 | Srinivasan et al. | |
| 2005/0154369 A1 | 7/2005 | Broullette et al. | |
| 2007/0219480 A1* | 9/2007 | Kamen | A61M 5/14212 604/20 |
| 2011/0092898 A1 | 4/2011 | Chuang | |
| 2011/0230826 A1 | 9/2011 | Yoh et al. | |
| 2012/0271221 A1 | 10/2012 | Uhland et al. | |
| 2014/0305969 A1* | 10/2014 | Dittrich | B67D 1/0017 222/135 |
| 2015/0151074 A1* | 6/2015 | Hermez | A61M 16/0875 128/203.27 |

FOREIGN PATENT DOCUMENTS

| | | |
|---|---|---|
| CN | 103501847 | 1/2014 |
| CN | 104334226 | 2/2015 |
| EP | 2514477 | 10/2012 |
| JP | 2005-503899 | 2/2005 |
| JP | 2006-524120 | 10/2006 |
| JP | 2012-223562 | 11/2012 |
| WO | WO 2003/028797 | 4/2003 |
| WO | WO 2003/086510 | 10/2003 |
| WO | WO 2004/022138 | 3/2004 |
| WO | WO 2004/093818 | 11/2004 |
| WO | WO 2007/034229 | 3/2007 |
| WO | WO 2013/078257 | 5/2013 |

OTHER PUBLICATIONS

International Search Report and Written Opinion in International Appln. No. PCT/EP2017/084143, dated May 2, 2018, 14 pages.

* cited by examiner

MEDICAMENT DELIVERY DEVICE

CROSS REFERENCE TO RELATED APPLICATIONS

The present application is the national stage entry of International Patent Application No. PCT/EP2017/084143, filed on Dec. 21, 2017, and claims priority to Application No. EP 16206615.3, filed on Dec. 23, 2016, the disclosures of which are incorporated herein by reference.

TECHNICAL FIELD

The disclosure relates to a device for delivery of medicament to a patient.

BACKGROUND

Needle-based medicament delivery devices are one of the most commonly used means for the administration of medicament to a patient. Despite significant advances, this type of devices still have disadvantages. One such disadvantage is that the use of a needle to inject medicament into the patient's skin unavoidably involves making a hole into the injection site, thereby causing tissue injury. In addition, it is known that the penetration of the injection needle into the skin can be painful for the patient, in particular for a child.

Patch pumps, such as insulin pumps used by Type 1 or Type 2 diabetes sufferers, are a particular type of needle-based medicament delivery devices. This type of devices are configured to automatically and periodically inject a fixed amount of insulin to the patient, by means of an hypodermic injection needle. One disadvantage is that the needle has to be permanently inserted into the patient's body. This may be unpleasant and uncomfortable for the patient and may lead to irritations and complications.

At least in certain embodiments, the present invention sets out to overcome or alleviate at least some of the problems mentioned above. In particular, the present invention sets out to provide a device for delivery of medicament which reduces the discomfort induced by the introduction and/or presence of a needle into the skin of the patient.

SUMMARY

Aspects of the present invention relate to a medicament delivery device.

According to a further aspect of the present invention, there is provided a medicament delivery device comprising a medicament receiving element, at least one fluid chamber having a fluid outlet configured to direct fluid vapour towards the medicament receiving element, a heating element for heating the fluid in the at least one fluid chamber, the device being configured such that, in use, the heating element heats the fluid in the at least one fluid chamber to at least partially evaporate the fluid so that the vapor pressure in the at least one fluid chamber increases until the fluid is expelled out of the at least one fluid chamber through the fluid outlet towards the medicament receiving element and entrains the medicament towards the patient's skin.

The fluid outlet may comprise a micro-nozzle.

The fluid outlet may comprise a non-return valve.

The heating element may be resistive and may be configured to receive pulses of electrical current to heat the fluid.

The at least one fluid chamber may comprise an insulating element to prevent heat dissipation.

The medicament delivery device may comprise a fluid reservoir and a fluid pump mechanism for pumping the fluid from the fluid reservoir to the at least one fluid chamber.

The medicament receiving element may comprise a porous member configured to retain the medicament and arranged such that, in use, medicament passes from the porous member towards the patient's skin when entrained in fluid expelled out of the fluid outlet of the at least one fluid chamber.

The medicament receiving element may comprise a distribution sieve arranged such that, in use, medicament passes through the distribution sieve towards the patient's skin when entrained in fluid expelled out of the fluid outlet of the at least one fluid chamber.

The medicament receiving element may comprise a chamber configured to receive the medicament, the chamber including a delivery portion for delivering the medicament from the chamber to the patient.

The medicament delivery device may comprise a plurality of fluid chambers.

The medicament delivery device may comprise a cartridge of medicament.

The medicament delivery device may comprise a processor for controlling the medicament delivery to the patient.

The medicament delivery device may be an insulin delivery device.

The medicament delivery device may comprise a blood glucose sensor configured to send data relating to the blood glucose of the patient to the processor so that the processor controls the insulin delivery to the patient.

In one embodiment, the medicament receiving element is gas permeable.

In one embodiment, the medicament delivery device is configured such that the fluid is expelled out of the at least one fluid chamber through the fluid outlet and passes through the medicament receiving element.

In one embodiment, the medicament delivery device is configured such that medicament is transported to the medicament delivery element and, subsequently, the heating element heats the fluid in the at least one fluid chamber to at least partially evaporate the fluid.

In one embodiment, the heating element is configured to increase in temperature to heat the fluid in the at least one fluid chamber.

According to a still further aspect of the present invention, there is provided a fluid chamber for use in a medicament delivery device as described above.

According to a yet further aspect of the present invention, there is provided a method of delivering a medicament, comprising using a medicament delivery device comprising a medicament receiving element, at least one fluid chamber having a fluid outlet configured to direct fluid vapour towards the medicament receiving element, and a heating element for heating the fluid in the at least one fluid chamber, the method comprising using the heating element to heat the fluid in the at least one fluid chamber to at least partially evaporate the fluid so that the vapor pressure in the at least one fluid chamber increases until the fluid is expelled out of the at least one fluid chamber through the fluid outlet towards the medicament receiving element and entrains the medicament towards the patient's skin.

The terms "drug" or "medicament" which are used interchangeably herein, mean a pharmaceutical formulation that includes at least one pharmaceutically active compound.

The term "medicament delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g. patch devices, autoinjectors, injection pen devices and spinal injection systems.

BRIEF DESCRIPTION OF THE FIGURES

Exemplary embodiments of the present invention are described with reference to the accompanying drawings, in which.

DETAILED DESCRIPTION

Embodiments of the present invention provide a medicament delivery device comprising a medicament receiving element, at least one fluid chamber having a fluid outlet configured to direct fluid vapour towards the medicament receiving element, a heating element for heating the fluid in the at least one fluid chamber, the device being configured such that, in use, the heating element heats the fluid in the at least one fluid chamber to at least partially evaporate the fluid so that the vapor pressure in the at least one fluid chamber increases until the fluid is expelled out of the at least one fluid chamber through the fluid outlet towards the medicament receiving element and entrains the medicament towards the patient's skin. Providing such a medicament delivery mechanism allows to avoid the use of an injection needle for delivering the medicament to the patient. Since no injection needle is needed, the medicament delivery does not require making a hole into the injection site and therefore avoids causing tissue injury, as well as pain and discomfort. In addition, irritations and complications that may occur due to the introduction and/or presence of a needle into the skin of the patient are avoided.

Figure 1A:
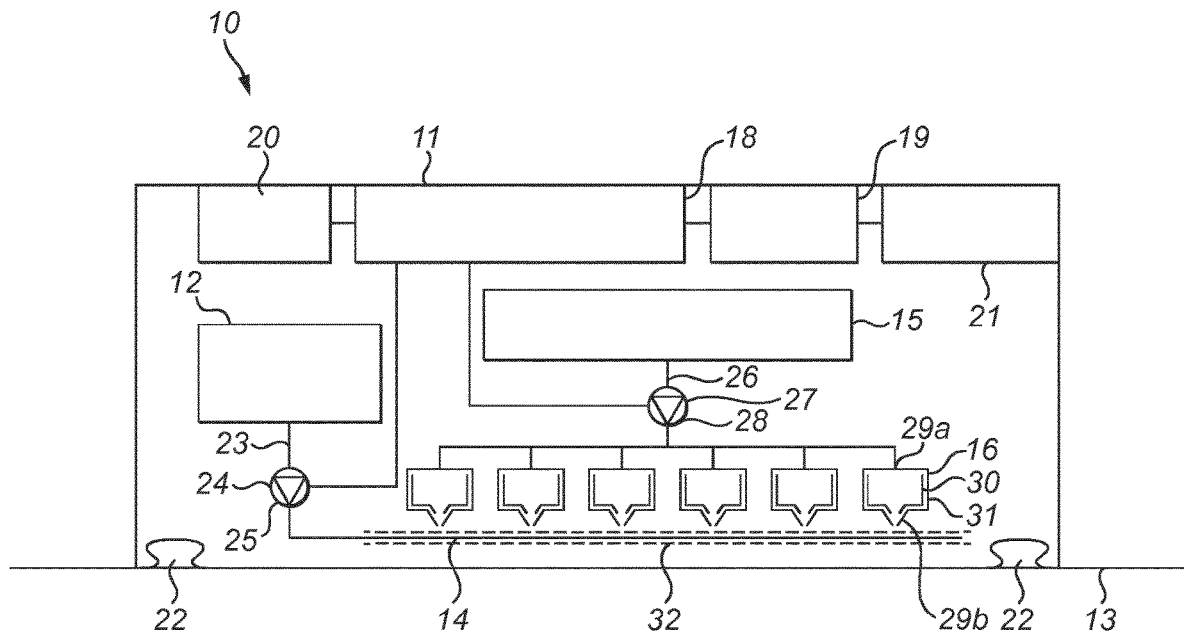
FIG. 1A shows a schematic cross-sectional view of an embodiment of the medicament delivery device in accordance with the present invention.
Figure 1B:
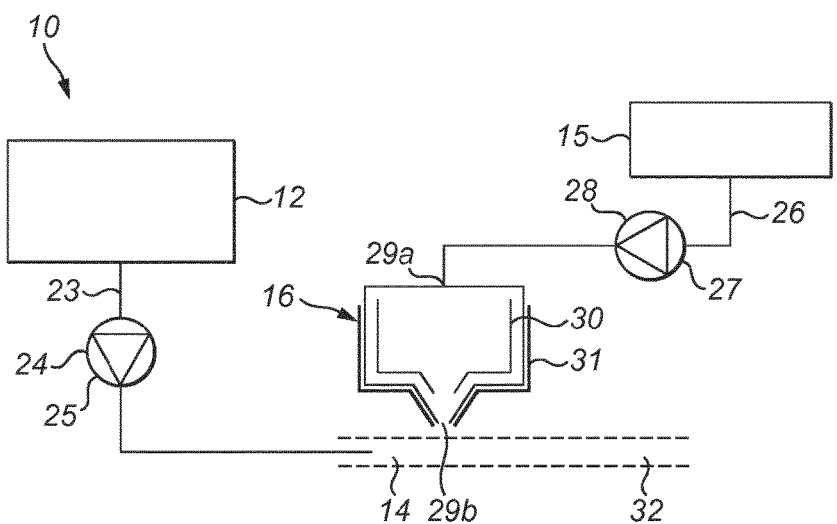
FIG. 1B shows a schematic cross-sectional view of a part of a variant of the medicament delivery device of FIG. 1A.

According to some embodiments of the present disclosure, an exemplary drug delivery device 10, herein simply referred to as "device 10", is shown in FIG. 1.

In the context of this application, the terms "proximal" and "distal" herein respectively refer to as relatively closer to the patient and relatively further away from the patient. Moreover, the terms "upstream" and "downstream" are used herein in relation to the direction of medicament flow and fluid flow through the device in normal use. Furthermore, the terms "vertically", "horizontally" and so forth are used herein in relation to the orientation of the device shown in the accompanying drawings.

The drug delivery device, as described herein, may be configured to inject a medicament into a patient. Such a device could be operated by a patient or care-giver, such as a nurse or physician. The device in accordance with certain aspects of the present invention includes a large volume device ("LVD") or patch pump, configured to adhere to a patient's skin for a period of time (e.g., about 5, 15, 30, 60, 120 minutes or longer) to deliver a "large" volume of medicament (typically about 2 ml to about 10 ml or more). As will be explained in more detail below, in the embodiment described herein, the medicament delivery device is configured to deliver medicament by repeated medicament discharges or "shots".

In combination with a specific medicament, the presently described device may also be customized in order to operate within required specifications. For example, the device may be customized to inject a medicament within a certain time period (e.g. about 10 minutes to about 60 minutes or longer). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP.

The delivery devices described herein can also include one or more automated functions. For example, the medicament injection can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of the present drug delivery device may each be activated via an activation mechanism. Such an activation mechanism can include one or more of a button, a lever, or other activation component. Activation of an automated function may be a one-step or multi-step process. That is, a user may need to activate one or more activation components in order to cause the automated function. For example, in a one-step process, a user may depress a button or interact with a user interface in order to cause injection of a medicament. Other devices may require a multi-step activation of an automated function.

Device 10 includes a body or housing 11 which typically contains a reservoir 12 pre-filled with liquid medicament to be injected, and the components required to facilitate one or more steps of the delivery process. Device 10 can also include a protective cover 13 that can be detachably mounted to the housing 11. Typically, when using the device 10 for the first time, a user must remove the protective cover 13 from the housing 11 before the device 10 can be operated.

As shown in FIG. 1, the device 10 includes a medicament retaining element or medicament receiving element 14 configured to receive medicament from the medicament reservoir 12. The device 10 also comprises a fluid reservoir 15 and a plurality of fluid chambers 16 configured to receive fluid from the fluid reservoir 15. The device 10 further comprises a processor 18 for monitoring and/or controlling the operation of the device 10 and a power supply 20, such as a disposable or rechargeable battery, or a power supply 20 configured to generate a pulsed current. The device 10 further comprises a user interface 19 and a wireless communication unit 21.

The device 10 is preferably a wearable device. Such devices are commonly referred to as "patch pumps" due to their nature of being worn or affixed to the user's skin. The device 10 comprises a device holding element 22 operating e.g. with vacuum to adhere the device 10 to the patient's skin. Alternatively, the holding element 22 may be in the form of an adhesive pad configured to adhere to the patient's skin. The adhesive pad is attached to the skin attachement side of the device 10 and covered by the protective cover 13 prior to the first use of the device 10.

In the device 10 described herein, the medicament receiving element 14 is in the form of distribution sieve, or mesh, or fleece 32. The distribution sieve 32 is arranged downstream of the fluid chambers 16. In use, the distribution sieve 32 is fed with medicament flowing from the medicament reservoir 12, and delivers droplets of medicament to the patient's skin. The protective cover 13 may be attached to the distribution sieve 32 prior to the first use of the device 10.

The device 10 comprises a medicament outflow line 23 through which medicament can flow, from the medicament reservoir 12 towards the distribution sieve 32. A medicament pump mechanism 24 is provided in the medicament outflow line 23 for pumping the medicament from the medicament reservoir 12 towards the distribution sieve 32. The medicament pump mechanism 24 comprises a non-return valve or check valve 25 for allowing the medicament to flow through the medicament outflow line 23 in only one direction, from the medicament reservoir 12 towards the distribution sieve 32.

The fluid reservoir 15 is adapted to receive and/or store a fluid intended to evaporate and entrain or propel the medicament through the distribution sieve 32 towards the patient's skin. The fluid used in the device 10 described herein is a liquid, e.g. sterile water. Water, used as the fluid to expel the medicament out of the device 10, has the advantage of being a neutral solution and not causing any side effect to the patient.

The fluid reservoir or water reservoir 15 is connected to the fluid chambers 16 by means of a fluid outflow line 26. A fluid pump mechanism 27 is provided in the fluid outflow line 26 for pumping the fluid from the fluid reservoir 15 to the fluid chambers 16. The fluid pump mechanism 27 comprises a non-return valve or check valve 28 for allowing the fluid to flow through the fluid outflow line 26 in only one direction, from the fluid reservoir 15 towards the fluid chambers 16.

The fluid chambers 16 are disposed downstream of the fluid reservoir 15 and upstream of the distribution sieve 32. The fluid chambers 16 are aligned horizontally with each other. A fluid chamber 16 includes a fluid inlet 29*a* and a fluid or steam outlet 29*b*. The fluid inlet 29*a* is arranged in an upper wall of the fluid chamber 16. The fluid outlet 29*b* is arranged in a bottom wall of the fluid chamber 16. The fluid outlet 29*b* extends substantially vertically from the fluid chamber 16. The fluid outlet 29*b* is configured to direct fluid vapour towards the distribution sieve 32. The fluid chambers 16 are similar to each other. The number of fluid chambers 16 in the device 10 depends on the quantity of fluid or medicament to be injected over time. In the embodiment where the device 10 is intended to be used for long-term administration of medicament such as insulin, the device may comprise a single fluid chamber 16 (as shown in FIG. 1B). In the embodiment where the device 10 is a large volume device ("LVD"), e.g. configured to deliver 10 ml or more of medicament in e.g. one hour, the device 10 may comprise two or more fluid chambers 16. In a preferred embodiment, the device 10 comprises two fluid chambers 16. In use, the device 10 may be positioned at several different locations on the patient's skin, to avoid any irritation of the patient's skin due repeated medicament injections at a same injection site. Moreover, the device 10 may be positioned at several different locations on the patient's skin in order to reduce the pain feeling due to the memory of the nerves, that may appear after repeated injections at a same injection site.

The fluid outlet 29*b* has a cross-sectional area substantially smaller than the cross-sectional area of the fluid chamber 16. In the device 10 described herein, the fluid outlet 29*b* is in the form of a micro-nozzle. Such a configuration for the fluid outlet 29*b* ensures that when the fluid evaporates in the fluid chamber 16, a surge of vapour pressure is produced within the fluid chamber 16. When the fluid evaporates in the fluid chamber 16, the vapour pressure in the fluid chamber 16 increases until reaching a threshold value at which the fluid vapour is ejected out of the fluid chamber 16 through the micro-nozzle and discharges abruptly in the distribution sieve 32. In other words, a water vapour explosion or steam blast occurs in the fluid chamber 16 when the vapour pressure reaches the threshold value in the fluid chamber 16, such that water steam is propelled out of the fluid chamber 16, through the fluid outlet 29*b*, into the distribution sieve 32.

A heating element 30 is provided for heating the fluid within the fluid chamber 16. The heating element 30 is arranged in the fluid chamber 16. The heating element 30 is arranged such that, in use, the heating element 30 is in contact with the water received in the fluid chamber 16. The heating element 30 is for example in the form of a resistive layer or mold arranged on a inner wall of the fluid chamber 16. In the embodiment described herein, the heating element 30 is configured to receive pulses of electrical current from the power supply 20 to heat the water in the fluid chamber 16. More generally, the heating element 30 is configured to heat the fluid discontinuously in the fluid chamber 16, to cause corresponding discontinuous surges of vapour pressure within the fluid chamber 16, and thereby corresponding medicament discharges towards the patient's skin.

To estimate the heating power needed to evaporate water in the fluid chamber 16, the following formula is used:

$$c = \frac{C}{m} = \frac{\Delta Q}{m \cdot \Delta T}$$

where ΔQ is the amount of energy transferred from the heating element 30 to the water, ΔT is the temperature difference, C is the heat capacity of water vapour, m is the mass of water heated and c is the mass heat capacity of water vapour. For example, heating a water droplet of 10 μL, during 1 second, using a temperature increase of 100K, requires a heating power of 4.18 W. Heating the same volume of water using the same temperature increase, during only 100 ms, requires 41.8 W. To have a heating power of 100 W, the device 10 can for example include a heating element 30 in the form of a resistor having a resistance of 0.25 Ohms at a voltage of 5 Volts.

The heating element 30 may be protected by an over temperature protection (not shown), such as a bimetal thermal protector or a temperature sensor combined with the appropriate electronic components.

The heating element 30 is arranged to optimally heat the water, with minimum thermal loss. To further minimize thermal losses, the fluid chambers 16 comprise an insulating element 31. The insulating element 31 is provided to prevent heat dissipation from the fluid chambers 16 and thereby enhances the efficiency of the heating of water in the fluid chamber 16. The insulating element 31 is for example in the form of an insulating layer provided on an outer wall of the fluid chamber 16, e.g. surrounding an outer wall of the fluid chamber 16.

The parameters of the medicament delivery can be adapted depending on the medicament to be delivered and depending on the patient which the medicament is to be delivered to. Specifically, and not exhaustively, the speed of the medicament flow through the distribution sieve 32, the size of the micro-nozzles, the water vapour temperature, and the quantity of water used, can be adapted depending on characteristics of the active ingredient of the medicament, e.g. the viscosity of the active ingredient, and depending on the patient, e.g. the type of the patient's skin etc . . . .

The processor 18 controls the wireless communication unit 21, which is configured to transmit and/or receive information to/from another device in a wireless fashion. Such transmission may for instance be based on radio transmission or optical transmission. In some embodiments, the wireless communication unit 21 is a Bluetooth transceiver. Alternatively, wireless communication unit 21 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

The device 10 may include a blood glucose sensor (not shown) configured to send data relating to the blood glucose of the patient to the processor 18. The processor 18 can therefore control the insulin delivery to the patient depending on e.g. the blood glucose level of the patient. For example, a blood glucose sensor as described in US20040162470A1 may be used.

The operation of the medicament injection device 10 in accordance with the present invention will now be described.

The device 10 can be pre-programmed, e.g. either by the manufacturing facility or a healthcare provider so that no additional user programming is required. The device 10 can be programmed to deliver drug to the patient at different rates for different times of day or under different conditions. For example, for a patient that needs a quantity of insulin of 2 mL maximum per day, the device 10 can be programmed to deliver 0.1 mL of insulin per hour during 20 hours, e.g. by performing four injections of 25 μL per hour.

An injection is performed as follows. In use, the user activates the device 10 via the user interface 19. The medicament is pumped by means of the medicament pump mechanism 24 from the medicament reservoir 12 through the medicament outflow line 23 towards the distribution sieve 32. Meanwhile, the sterile water is pumped by means of the fluid pump mechanism 27, from the fluid reservoir 15 through the fluid outflow line 26 towards the fluid chambers 16. The water enters the fluid chambers 16 via the fluid inlets 29a. Then, pulses of current are generated by the power supply 20 and circulate through the resistive heating elements 30. Consequently, the temperature of the heating elements 30 increases, and heat is transferred from the heating elements 30 to the water within the fluid chambers 16. As water is heated, water evaporates and the vapour pressure in the fluid chambers 16 increases. It should be noted that as water is heated and evaporates in the fluid chambers 16, water is sterilised again in the fluid chambers 16. The vapour pressure increases until reaching a threshold value at which the water vapour is ejected out of the fluid chambers 16 through the micro-nozzles 29b, discharges abruptly towards the distribution sieve 32, and entrains the medicament through the distribution sieve 32, towards the patient's skin.

The water streams propelled out of the fluid chambers 16 ensure that the medicament flow has a sufficient speed to overcome the skin barrier and penetrate deep enough into the patient's skin. The injection depth of the medicament into the patient's skin also depends on the diameter of the micro-nozzles forming the fluid outlets 29b. As an example, a micro-nozzle diameter of approximately 100 μm and a medicament flow travelling at around 100 m/s can achieve an injection depth of around 2 mm.

Moreover, as the vapour pressure of the water vapour decreases in the distribution sieve 32, the temperature of the stream decreases consequently. The liquid medicament being at room temperature, the temperature of the stream of medicament flowing out of the device 10 through the distribution sieve 32 is sufficiently low such that, during the injection, the patient does not feel discomfort due to the temperature of the medicament stream.

Although the device 10 of the first embodiment has been described as having a medicament receiving element 14 in the form of a distribution sieve, the invention is not intended to be limited to this particular type of device and other types of device are intended to fall within the scope of the invention. For example, in an alternative embodiment, the medicament receiving element comprises a porous member, e.g. a carrier web or an absorbent pad. The absorbent pad is arranged downstream of the fluid chambers and is adapted to retain the medicament by absorption. In use, the absorbent pad is fed with medicament flowing from the medicament reservoir. The water vapour expelled out of the fluid chambers through the fluid outlet flows through the absorbent pad where it contacts the medicament and entrains the medicament towards the patient's skin. In a further alternative embodiment, the medicament receiving element comprises both the absorbent pad and the distribution sieve. The absorbent pad is disposed above the distribution sieve. The absorbent pad and the distribution sieve are disposed downstream of the fluid chambers. In use, the water vapour which is expelled out of the fluid chambers through the fluid outlet flows into the absorbent pad where it contacts the medicament and entrains the medicament through the distribution sieve, towards the patient's skin.

Figure 2:
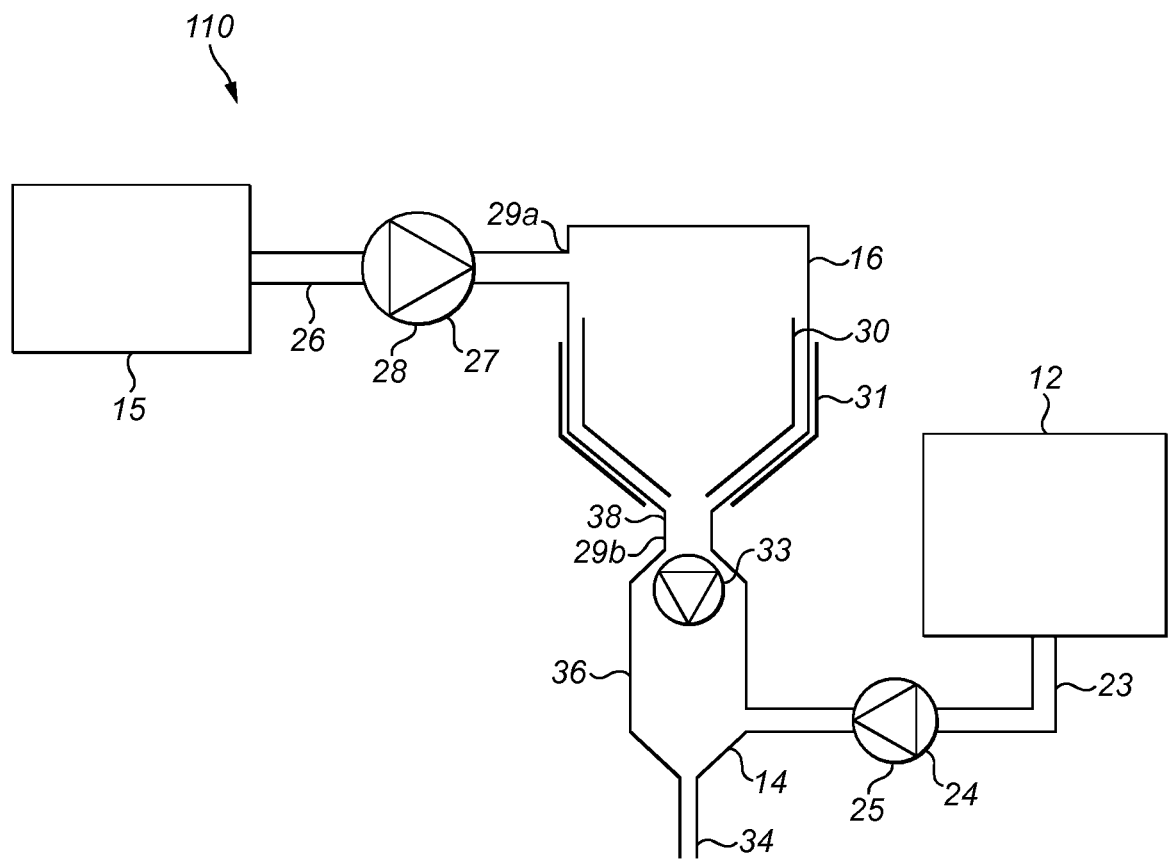
FIG. 2 shows a schematic cross-sectional view of a part of a further embodiment of the medicament delivery device in accordance with the present invention.

A medicament delivery device 110 of a second embodiment is shown in FIG. 2 and is similar to the device 10 of the first embodiment. Like features retain the same reference numerals and a detailed description of such like features will not be repeated.

A difference with the device 110 of the second embodiment over the device 10 of the first embodiment is that, in the device 110 of the second embodiment, the device 110 comprises a single fluid chamber 16. However, in a variant, the device 110 could comprise two or more fluid chambers 16.

Figure 3:
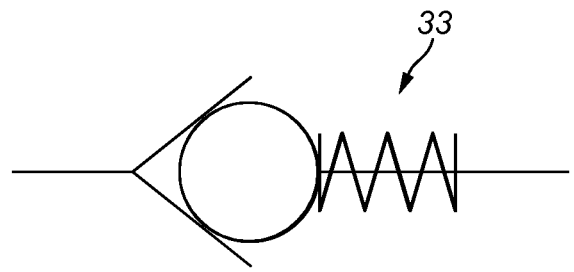
FIG. 3 shows a schematic view of a valve used in the medicament delivery device of FIG. 2.

An additional difference with the device 110 of the second embodiment over the device 10 of the first embodiment is that, in the device 110 of the second embodiment, the fluid inlet 29a is arranged in a side wall of the fluid chamber 16. In addition, the medicament receiving element 14 is in the form of a chamber 36 connected to the steam outlet 29b, downstream of the steam outlet 29b. The chamber 36 comprises a delivery portion in the form of a dispensing nozzle 34 extending downwards from the chamber 36. The dispensing nozzle 34 may be a micro-nozzle. The dispensing nozzle 34 not only provides an orifice through which the medicament flows out of the device 110, but also provides a surface which contacts the patient's skin. The fluid outlet 29b is in the form of a passage of reduced diameter, thereby forming a venturi passage or venturi nozzle 38. A non-return valve or check valve 33, for example a spring-tensioned ball check valve (represented in FIG. 3) is disposed in the venturi nozzle 38. The check valve 33 ensures that the water vapour does not leak from the fluid chamber 16 before the vapour pressure reaches the threshold value. The check valve 33 can be adjusted such that the medicament stream flowing through the dispensing nozzle 34 has a sufficient speed when flowing towards the patient's skin. In an alternative embodiment, the fluid outlet 29b comprises a solenoid valve in combination with a pressure sensor. Such alternative arrangement provides the advantage that the steam flow through the fluid outlet 29b is easy to control.

In the device 110, the water vapour cools down while flowing in the chamber 36. This decrease of temperature allows for an efficient mixing of the water and the medicament, thereby allowing an efficient transport of the medicament out of the device 110 towards the patient's skin.

Figure 4:
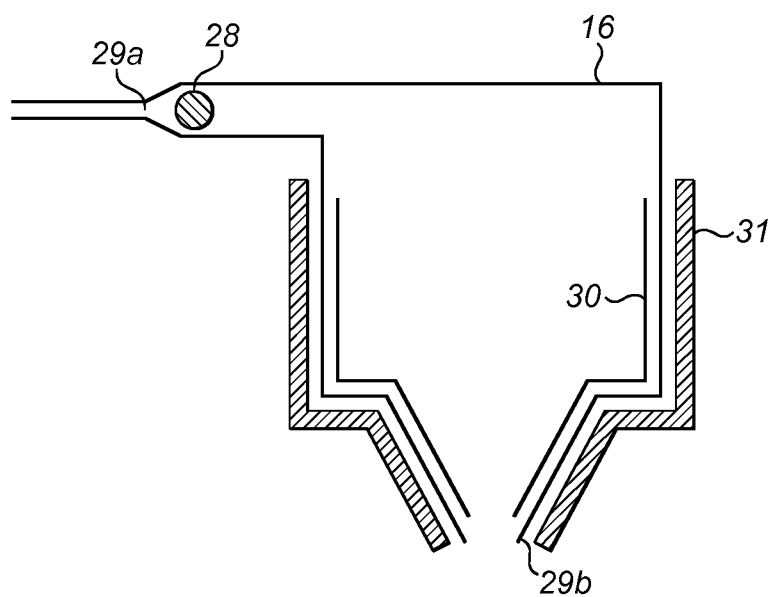
FIG. 4 shows a schematic cross-sectional view of a variant of a fluid chamber used in the medicament delivery device in accordance with the present invention.

Although the devices 10, 110 of the first and second embodiments have been described as having a fluid pump mechanism 27 disposed in the fluid outflow line 26, the invention is not intended to be limited to this particular type of device and other types of device are intended to fall within the scope of the invention, for example devices in which the fluid pump mechanism 27 is disposed in the fluid inlet 29a of the fluid chambers 16, as represented in FIG. 4.

Although the fluid chambers of the first and second embodiments 10, 110 each comprise a single fluid outlet, the invention is not intended to be limited to this particular type of fluid chambers and other types of fluid chambers are intended to fall within the scope of the invention, for example fluid chambers having two or more fluid outlets.

The devices 10, 110 include a medicament reservoir 12 pre-filled with medicament. However, the invention is not intended to be limited to this particular type of device and other types of device are intended to fall within the scope of the invention, for example devices comprising a cartridge holder for receiving a cartridge of medicament that may be changed between two consecutive uses of the device, or when the cartridge is empty.

The medicament reservoir 12 and the fluid reservoir 15 are refillable such that the devices 10, 100 are reusable. However, the invention is not intended to be limited to this particular type of device and other types of device are intended to fall within the scope of the invention, for example devices which are fully disposable, or devices which include a disposable part, e.g. a disposable medicament cartridge and/or a disposable fluid reservoir, and a reusable part, e.g. the remainder of the device.

In the above described embodiments, the heating element 30 comprises a resistive heating element. However, it should be recognised that in alternative embodiments (not shown) the heating element may have a different arrangement. For example, the heating element may comprise a thermoelectric controller, such as a Peltier controller, that is configured to heat the fluid in the fluid chamber. In another embodiment, the heating element is configured to heat the fluid in the fluid chamber via combustion. For instance, the heating element may comprise a fuel source, for example, a gas such as propane, which is ignited to heat the fluid in the fluid chamber. In another embodiment, the heating element emits radiation to heat the fluid in the fluid chamber. In one embodiment, the heating element comprises a laser that irradiates a surface of the fluid chamber to heat the fluid.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., pen injector, auto injector, large-volume device, pump, perfusion system, or other device configured for intraocular, subcutaneous, intramuscular, or intravascular delivery), skin patch (e.g., osmotic, chemical), inhaler (e.g., nasal or pulmonary), an implantable device (e.g., drug- or API-coated stent, capsule), or a feeding system for the gastro-intestinal tract.

The drug or medicament may be contained in a primary package or "drug container" adapted for use with a drug delivery device. The drug container may be, e.g., a cartridge, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about 4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing.

Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament delivery device comprising:
   a medicament receiving element configured to directly receive a medicament from a medicament reservoir;
   at least one fluid chamber having a fluid outlet configured to direct fluid vapor towards the medicament receiving element; and
   a heating element for heating a fluid in the at least one fluid chamber,
   wherein the medicament delivery device is configured such that, in use, the heating element heats the fluid in the at least one fluid chamber to at least partially evaporate the fluid so that vapor pressure in the at least one fluid chamber increases until reaching a threshold value at which the fluid vapor is expelled out of the at least one fluid chamber through the fluid outlet towards the medicament receiving element and the fluid vapor entrains the medicament and directs the medicament towards a patient's skin.

2. The medicament delivery device according to claim 1, wherein the fluid outlet comprises a micro-nozzle.

3. The medicament delivery device according to claim 1, wherein the fluid outlet comprises a non-return valve.

4. The medicament delivery device according to claim 1, wherein the heating element is resistive and is configured to receive pulses of electrical current to heat the fluid.

5. The medicament delivery device according to claim 1, wherein the at least one fluid chamber comprises an insulating element to prevent heat dissipation.

6. The medicament delivery device according to claim 1, comprising a fluid reservoir and a fluid pump mechanism for pumping the fluid from the fluid reservoir to the at least one fluid chamber.

7. The medicament delivery device according to claim 1, wherein the medicament receiving element comprises a porous member configured to retain the medicament and arranged such that, when the medicament delivery device is in use and when the medicament is entrained in fluid vapor expelled out of the fluid outlet of the at least one fluid chamber, the medicament passes from the porous member towards the patient's skin.

8. The medicament delivery device according to claim 1, wherein the medicament receiving element comprises a distribution sieve arranged such that, when the medicament delivery device is in use and when the medicament is entrained in fluid expelled out of the fluid outlet of the at least one fluid chamber, the medicament passes through the distribution sieve towards the patient's skin.

9. The medicament delivery device according to claim 1, wherein the medicament receiving element comprises a chamber configured to receive the medicament, the chamber including a delivery portion for delivering the medicament from the chamber to the patient.

10. The medicament delivery device according to claim 1, wherein the at least one fluid chamber is a plurality of fluid chambers.

11. The medicament delivery device according to claim 1, comprising a cartridge containing the medicament.

12. The medicament delivery device according to claim 1, comprising a processor for controlling delivery of the medicament to the patient.

13. The medicament delivery device according to claim 1, wherein the medicament receiving element is gas permeable.

14. The medicament delivery device according to claim 1, wherein the medicament delivery device is configured such that the fluid is expelled out of the at least one fluid chamber through the fluid outlet and passes through the medicament receiving element.

15. The medicament delivery device according to claim 1, wherein the medicament delivery device is configured such that the medicament is transported to the medicament receiving element and, subsequently, the heating element heats the fluid in the at least one fluid chamber to at least partially evaporate the fluid.

16. The medicament delivery device according to claim 1, wherein the medicament delivery device is an insulin delivery device.

17. The medicament delivery device according to claim 16, comprising:
   a processor for controlling medicament delivery to the patient; and
   a blood glucose sensor configured to send data relating to blood glucose of the patient to the processor so that the processor controls insulin delivery to the patient.

18. A fluid chamber for use in a medicament delivery device, the fluid chamber comprising:
   a fluid outlet configured to direct fluid vapor towards a medicament receiving element of the medicament delivery device, the medicament receiving element being configured to directly receive a medicament from a medicament reservoir; and a heating element for heating a fluid in the fluid chamber, the heating element configured to heat the fluid in the fluid chamber to at least partially evaporate the fluid so that vapor pressure in the fluid chamber increases until reaching a threshold value at which the fluid vapor is expelled out of the fluid chamber through the fluid outlet towards the medicament receiving element of the medicament delivery device and the fluid vapor entrains the medicament and directs the medicament towards a patient's skin.

19. A method of delivering a medicament, the method comprising heating a fluid in at least one fluid chamber of a medicament delivery device to at least partially evaporate the fluid so that vapor pressure in the at least one fluid chamber increases until reaching a threshold value at which the fluid vapor is expelled out of the at least one fluid chamber towards a medicament receiving element of the medicament delivery device, the medicament receiving element being configured to directly receive the medicament from a medicament reservoir, and the fluid vapor entrains the medicament and directs the medicament towards a patient's skin.

* * * * *